(12) United States Patent
Ornstein et al.

(10) Patent No.: US 6,720,357 B2
(45) Date of Patent: Apr. 13, 2004

(54) SULFONAMIDE DERIVATIVES

(75) Inventors: Paul Leslie Ornstein, Carmel, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/258,054

(22) PCT Filed: May 4, 2001

(86) PCT No.: PCT/US01/11746

§ 371 (c)(1), (2), (4) Date: Oct. 17, 2002

(87) PCT Pub. No.: WO01/90056

PCT Pub. Date: Nov. 29, 2001

(65) Prior Publication Data

US 2003/0233015 A1 Dec. 18, 2003

Related U.S. Application Data

(60) Provisional application No. 60/205,822, filed on May 19, 2000.

(51) Int. Cl.⁷ .................. C07C 311/03; A61K 31/18
(52) U.S. Cl. .......................... 514/605; 564/99
(58) Field of Search ............... 564/99; 514/605

(56) References Cited

FOREIGN PATENT DOCUMENTS

| | | | |
|---|---|---|---|
| EP | 0 860 428 | * | 8/1998 |
| WO | WO 98/33496 | | 2/1997 |
| WO | WO 00/06148 | | 7/1998 |
| WO | WO 00/06156 | | 7/1998 |
| WO | WO 00/06158 | | 7/1998 |
| WO | WO 00/06537 | | 7/1998 |

OTHER PUBLICATIONS

U.S. patent application Ser. No. 60/329,056, Bleakman et al., filed Oct. 12, 2001.

* cited by examiner

*Primary Examiner*—Peter O'Sullivan
(74) *Attorney, Agent, or Firm*—John A. Cleveland, Jr.; Nelsen L. Lentz

(57) ABSTRACT

The present invention relates to a compound of formula (Ia) or a pharmaceutically acceptable salt thereof which is useful for the treatment of conditions associated with glutamate hypofunction, such as psychiatric and neurological disorders.

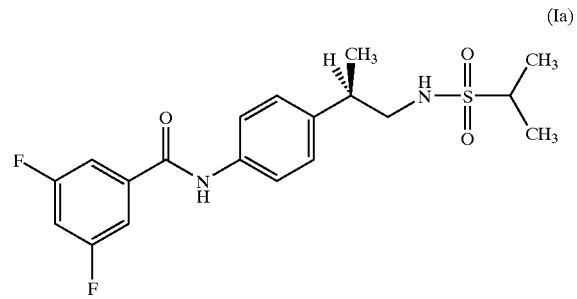

(Ia)

15 Claims, No Drawings

SULFONAMIDE DERIVATIVES

This is the national phase application, under 35 USC 371, for PCT/US01/11746 filed May 4, 2001, which claims the priority of U.S. Provisional Application No. 60/205,822 filed May 19, 2000.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EM receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term is potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in PharmacoL Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Phannacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993.

International Patent Application Publication WO 98/33496 published Aug. 6, 1998 discloses certain sulfonamide derivatives which are useful, for example, for treating psychiatric and neurological disorders, for example cognitive disorders; neuro-degenerative disorders such as Alzheimer's disease; age-related dementias; age-induced memory impairment; movement disorders such as tardive dyskinesia, Huntington's chorea, myoclonus, and Parkinson's disease; reversal of drug-induced states (such as cocaine, amphetamines, alcohol-induced states); depression; attention deficit disorder; attention deficit hyperactivity disorder; psychosis; cognitive deficits associated with psychosis, and drug-induced psychosis.

The present invention provides compounds of formula 1:

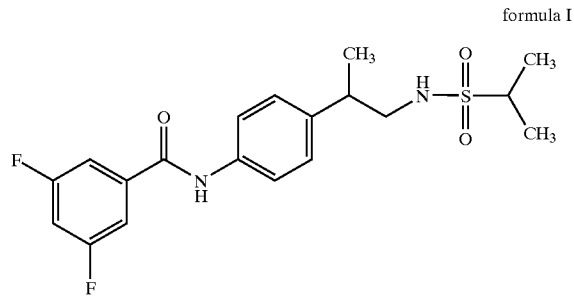

formula I or a pharmaceutically acceptable salt thereof.

The present invention further provides a compound of formula Ia:

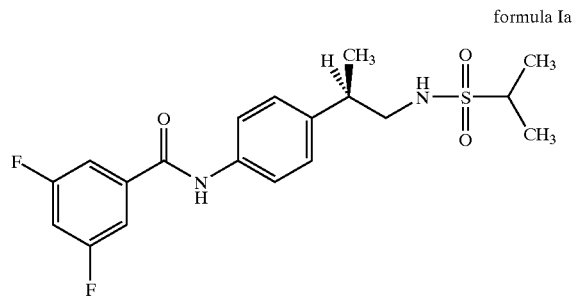

formula Ia or a pharmaceutically acceptable salt thereof.

The present invention further provides a method of potentiating glutamate receptor function in a patient which comprises administering to said patient an effective amount of a compound of formula Ha.

In addition, the present invention provides a method of treating depression in a patient comprising administering to said patient an effective amount of a compound of formula Ia.

The present invention further provides a method of treating schizophrenia in a patient comprising administering to said patient an effective amount of a compound of formula Ia.

Furthermore, the present invention provides a method of treating cognitive disorders in a patient comprising administering to said patient an effective amount of a compound of formula Ia.

The invention further provides pharmaceutical compositions of compounds of formula Ia, including the hydrates thereof, comprising, as an active ingredient, a compound of formula Ia in combination with a pharmaceutically acceptable carrier, diluent or excipient.

This invention also encompasses novel intermediates, and processes for the synthesis of the compounds of formula Ia.

In addition, the present invention provides the use of a compound of formula Ia or a pharmaceutically acceptable salt thereof for potentiating glutamate receptor function.

According to another aspect, the present invention provides the use of a compound of formula Ia for the manufacture of a medicament for potentiating glutamate receptor function.

The present invention further provides an article of manufacture comprising packaging material and a compound of formula Ia or a pharmaceutically acceptable salt thereof contained within said packaging material, wherein said packaging material comprises a label which indicates that said compound of formula Ia can be used for treating at least one of the following; Alzheimer's disease, schizophrenia, cognitive deficits associated with schizophrenia, depression, and cognitive disorders.

DETAILED DESCRIPTION OF THE INVENTION

In this specification, the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders; neuro-degenerative disorders such as Alzheimer's disease; age-related dementias; age-induced memory impairment; movement disorders such as tardive dyskinesia, Huntington's chorea, myoclonus, dystonia, and Parkinson's disease; reversal of drug-induced states (such as cocaine, amphetamines, alcohol-induced states); depression; attention deficit disorder; attention deficit hyperactivity disorder; psychosis; cognitive deficits associated with psychosis, and drug-induced psychosis. In addition, the compounds of formula I are useful for treating sexual dysfunction. The compounds of formula I may also be useful for improving memory (both short term and long term) and learning ability. The present invention provides the use of compounds of formula I for the treatment of each of these conditions.

It is understood by one of ordinary skill in the art that the compound of formula Ia:

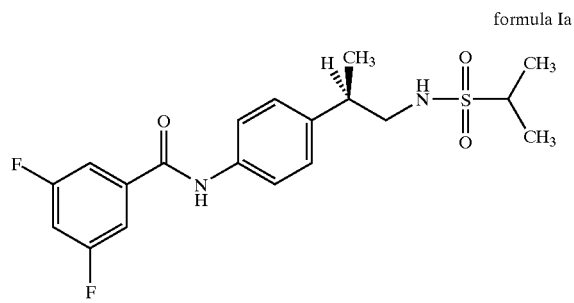

formula Ia is included within the scope of formula I defined hereinabove. More specifically, formula I is a racemic mixture and formula Ia is the corresponding (R)-enantiomer.

The present invention includes the pharmaceutically acceptable salts of the compounds defined by formula I and formula Ia. The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable organic or inorganic base. Such salts are known as base addition salts. Such salts include the pharmaceutically acceptable salts listed in *Journal of Pharmaceutical Science*, 66, 2–19 (1977) which are known to the skilled artisan.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" referes to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein the term "Lg" refers to a suitable leaving group. Examples is of suitable leaving groups are Cl, Br, and the like.

The compounds of formula I can be prepared, for example, following analogous procedures set forth in International Patent Application Publication WO 98/33496 published Aug. 6, 1998 (See Example 196 therein). More specifically, the compounds of formula I and formula Ia can be prepared, for example, as disclosed in Scheme I. The reagents and starting materials are readily available to one of ordinary skill in the art. All substituents, unless otherwise specified are as previously defined.

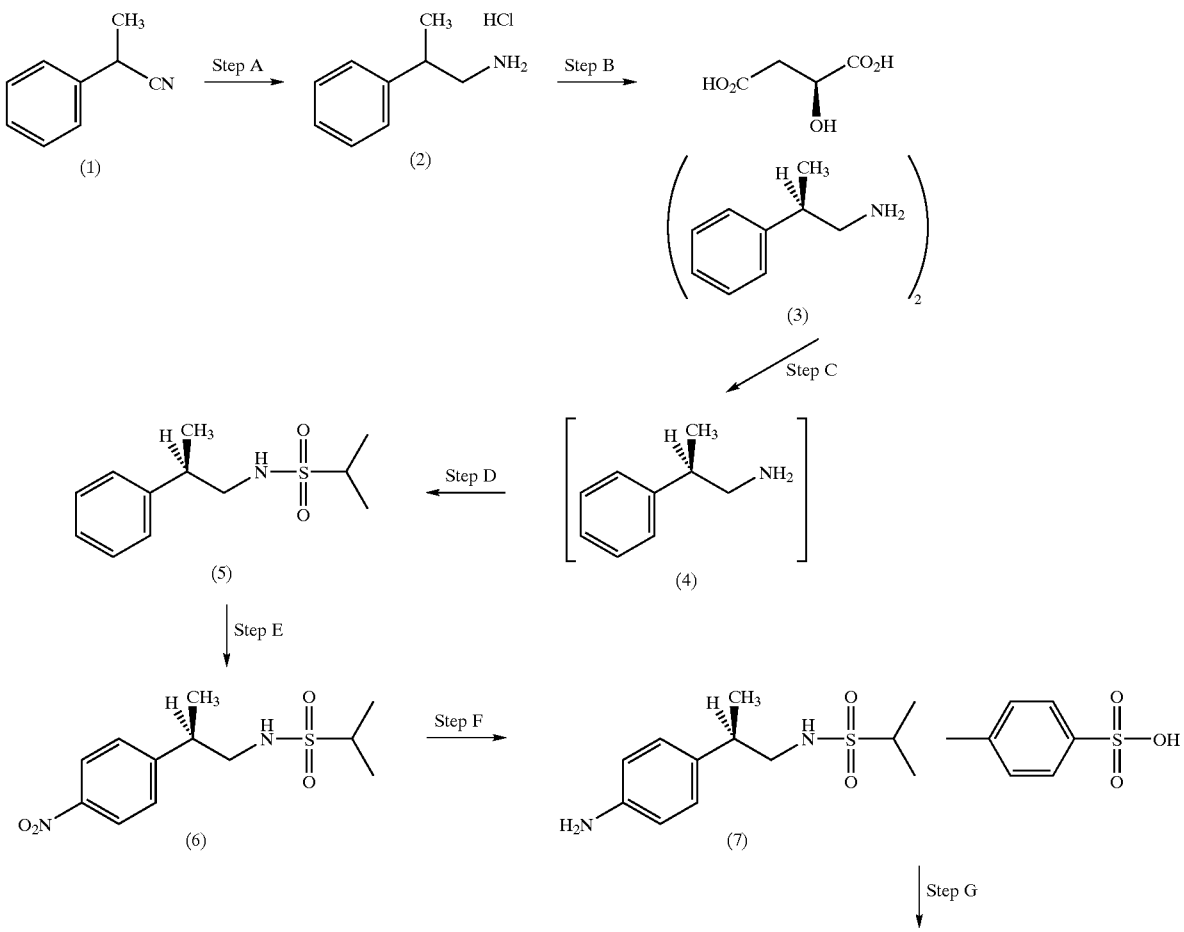

Scheme I

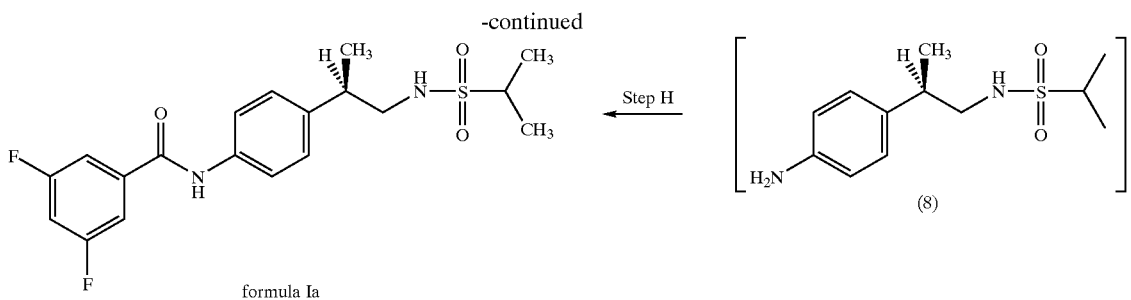

formula Ia

In Scheme I, step A, the nitrile (1) is hydrogenated to provide the primary amine (2) as the HCl salt. For example, nitrile (1) is dissolved in a suitable organic solvent, such as ethanol, treated with a suitable hydrogenation catalyst, such as palladium on carbon, treated with concentrated HCl and placed under hydrogen at a pressure and temperature sufficient to effect reduction of the nitrile (1) to the primary amine (2). The reaction is then filtered and the filtrate concentrated to provide crude primary amine (2) as the HCl salt. This crude material is then purified by techniques well known in the art, such as recrystallization from a suitable solvent.

In Scheme I, step B, the primary amine (2) HCl salt can be treated with a suitable resolving agent to provide the salt (3). For example, the primary amine (2) HCl salt is dissolved in a suitable organic solvent, such as ethanol and treated with about an equivalent of a suitable base, such as sodium hydroxide. The reaction is filtered and the filtrate is treated with a suitable resolving agent, such as L-malic acid. For example, about 0.25 equivalents of L-malic acid in a suitable organic solvent, such as ethanol is added to the filtrate. The solution is then heated to about 75° C. and stirred for about 30 minutes. The solution is then allowed to cool slowly with stirring. The precipitate is then collected by filtration, rinsed with ethanol and dried under vacuum to provide the salt (3). The salt (3) is then suspended in a suitable organic solvent, such as ethanol and water is added. The slurry is heated at reflux until the solids go into solution. The solution is then allowed to cool slowly with stiring for about 8 to 16 hours. The suspension is further cooled to about 0 to 5° C. and the salt (3) is collected by filtration. The salt (3) is then rinsed with ethanol and dried at about 35° C.

In Scheme I, step C, salt (3) is converted to the free base (4) and in Step D, free base (4) is sulfonylated to provide sulfonamide (5). For example, salt (3) is slurried in a suitable organic solvent, such as methylene chloride and treated with about 2 equivalents of a suitable base, such as aqueous sodium hydroxide. The mixture is stirred for about one hour and the organic phase is separated. The organic phase is then dried, for example by azeotropic distallation with heptane to provide the free base (4). The dried free base (4) in heptane is then treated, for example, with a catalytic amount of 4-dimethylaminopyridine, an excess of triethylamine and methylene chloride is added to provide total dissolution. The solution is cooled to about 5° C. and treated with about one equivalent of a compound of formula Lg—SO₂CH(CH₃)₂, such as isopropylsulfonyl chloride. The reaction is then allowed to warm to room temperature over about 16 hours. The reaction is then cooled to about 8° C. and treated with 2N aqueous HCl. The organic phase is then separated and washed with water, sodium bicarbonate, dried over anhydrous sodium sulfate, filtered, and concentrated under vacuum to provide sulfonamide (5).

In Scheme I, step E, sulfonamide (5) is nitrated to provide the p-nitro derivative (6). More specifically, sulfonamide (5) is combined with trifluoroacetic acid in a suitable organic solvent mixture, such as methylene chloride and heptane. The mixture is cooled to about −5° C. and about 1.2 equivalents of 98% fuming nitric acid is added to the mixture. The reaction is then stirred at about −5° C. to 5° C. for about 3 to about 5 hours and then warmed to room temperature. The reaction mixture is then diluted with methylene chloride and water, and mixed for about 15 minutes. The aqueous phase is then separated and extracted with methylene chloride. The organic phase and organic extracts are combined, treated with water and aqueous base, such as 10% sodium hydroxide. The pH is adjusted to about 6.5 to about 7.5 with saturated sodium carbonate. The mixture is stirred for about 10 to 15 minutes and the organic layer is separated. The organic layer is then concentrated under vacuum to provide crude p-nitro derivative (6) which is carried on directly to step F.

In Scheme I, step F, p-nitro derivative (6) is reduced to the p-amino derivative (7) and isolated as a suitable salt, such as a p-toluenesulfonate salt. More specifically, crude p-nitro derivative (6) is dissolved inethanol, treated with a suitable hydrogenation catalyst, such as palladium on carbon and placed under hydrogen at a pressure sufficient to effect reduction of the p-nitro derivative (6) to the p-amino derivative (7). The reaction is filtered, the filtrate concentrated under vacuum, and the crude p-amino derivative (7) is dissolved in a suitable organic solvent, such as tetrahydrofuran. To this solution is added an equivalent of a suitable acid, such as p-toluenesulfonic acid monohydrate with stirring. To this solution is then added MTBE and the slurry is stirred for about 1 to 2 hours. The slurry is then filtered and rinsed with MTBE/THF (3:1) to provide purified p-amino derivative (7).

In Scheme I, step G, the p-amino derivative (7) is converted to the corresponding free base (8). For example, p-amino derivative (7) is suspended in a suitable organic solvent, such as methylene chloride and treated with a suitable base, such as saturated aqueous sodium bicarbonate until the pH of the aqueous phase is about 6.5. The phases are separated, and the organic phase is rinsed with 5% sodium bicarbonate, water, and then concentrated under vacuum to provide free base (8). To this is added diethyl ether, or more preferably, methyl t-butyl ether, to effect crystallization. The resulting solid is collected by filtration to provide purified free base (8).

In Scheme I, step H, free base (8) is treated with a 3,5-dibenzoyl chloride to provide the compound of formula Ia. For example, free base (8) is combined with about 1.15 equivalents triethylamine in a suitable organic solvent, such as methylene chloride. About 1.1 equivalents of 3,5-difluorobenzoyl chloride is added to the solution at room temperature and stirred forabout 1 hour. The reaction mixture is then washed with water and dilute aqueous acid. The organic phase is then diluted with acetone and washed with saturated potassium carbonate, dilute aqueous acid, dried over anhydrous magnesium sulfate, filtered and concentrated under vacuum with addition of ethyl acetate. The residue is crystallized by addition of a suitable organic solvent, such as ethyl acetate. The resulting solids are collected by filtration and dried under vacuum to provide the compound of formula Ia.

In addition, step B can be skipped and the primary amine (2) HCl salt can be carried on directly to step D after converting it to the free base. In this manner the compound of formula I is ultimately prepared.

Alternatively, the compounds of formula Ia can also be prepared, for example, as further disclosed in Scheme II. The reagents and starting materials are readily available to one of ordinary skill in the art. All substituents, unless otherwise specified are as previously defined.

and treated with 0.5 equivalents of a suitable resolving agent, such as S-(–)-α-methylbenzylamine. The reaction mixture is then heated at reflux for about 10 minutes and then cooled to room temperature with stirring over about 8 hours to about 16 hours. The resulting precipitate is collected by filtration to provide crude salt (10). The crude salt (10) is reslurried in ethyl acetate at reflux for about 10 minutes and then cooled to room temperature with stirring over about 8 hours to about 16 hours. The salt (10) is collected by filtration, and the above reslurrying process is repeated. The collected salt (10) is then dried under vacuum.

In Scheme II, step B, the salt (10) is treated with aqueous acid under standard conditions well known to one of ordinary skill in the art to provide the free acid (11). For example salt (10) is combined with a suitable organic solvent, such as methylene chloride and treated with 1N HCl. After stirring

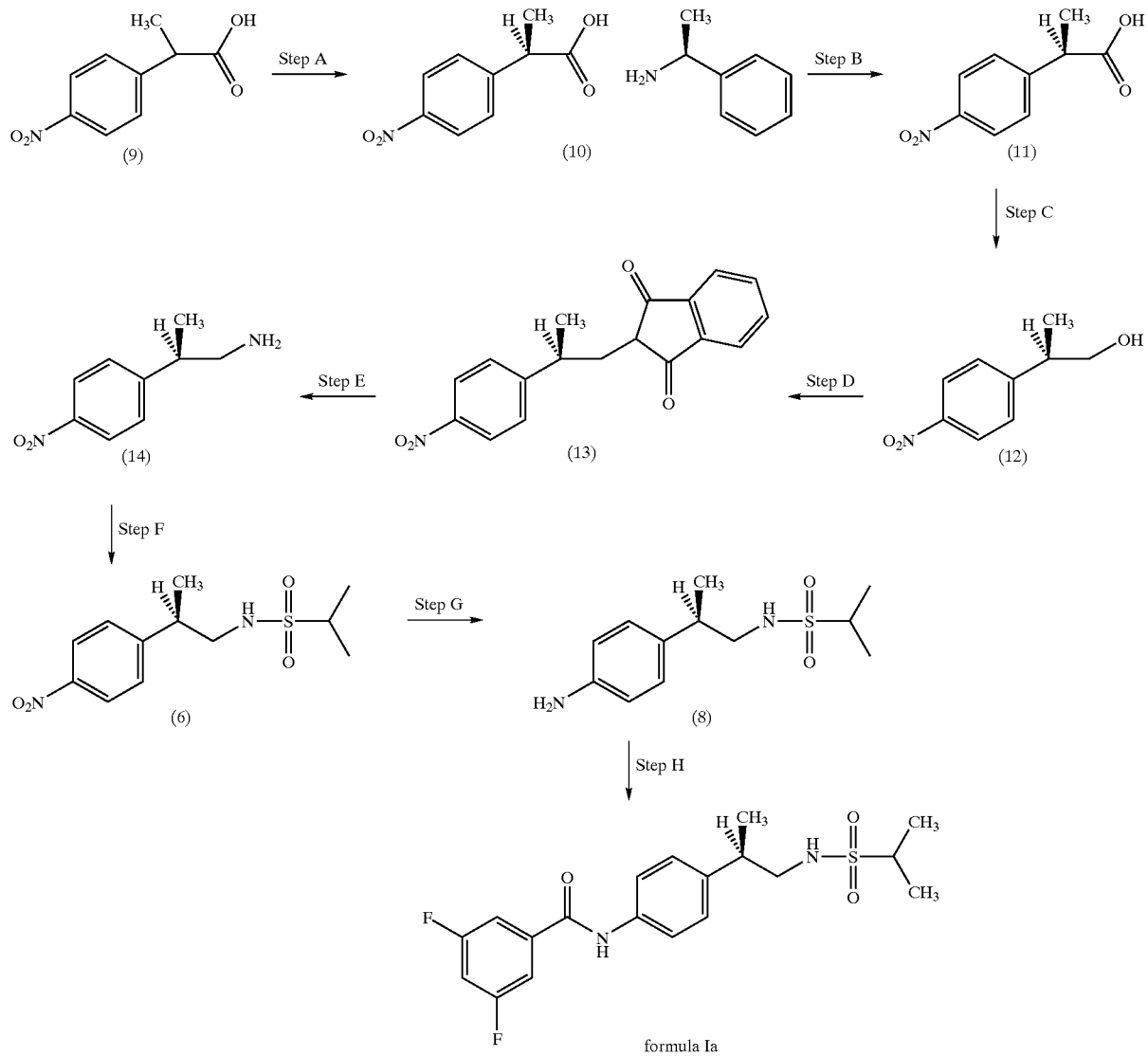

In Scheme II, step A, the acid (9) can be treated with a suitable resolving agent to provide the salt (10). For example, acid (9) is dissolved in a suitable organic solvent, such as ethyl acetate, the solution is heated to about 30° C.

the reaction mixture for about 1 to about 3 hours, the layers are separated, the organic layer is dried over anhydrous magnesium sulfate, filtered, and concentrated under vacuum to provide free acid (11).

In Scheme II, step C, acid (11) reduced with a suitable reducing agent to provide the primary alcohol (12). For example, acid (11) is dissolved in a suitable organic solvent, such as tetrahydrofuran and treated with a suitable reducing agent, such as borane dimethylsulfide. The reaction is then heated at reflux for about 5 hours, cooled to room temperature and quenched with saturated potassium carbonate. The reaction mixture is then stirred for about 3 hours and the top organic layer is separated. The aqueous layer is extracted with a suitable organic solvent, such as methylene chloride. The organic layer and organic extracts are combined, washed with saturated brine, dried over anhydrous magnesium sulfate, filtered, and concentrated under vacuum to provide the primary alcohol (12).

In Scheme II, step D, primary alcohol (12) is converted to the phthalimide derivative (13). For example, primary alcohol (12) is combined with about one equivalent of phthalimide and about 1.5 equivalents triphenylphosphine in a suitable organic solvent, such as tetrahydrofuran. To this solution is added about 1.5 equivalents of diethyl azodicarboxylate. The reaction mixture is then stirred for about 8 hours to about 16 hours, quenched with water and extracted with a suitable organic solvent, such as methylene chloride. The organic extracts are combined, dried over anhydrous magnesium sulfate, filtered, and concentrated under vacuum. The residue purified by running through a plug of silica gel with a suitable eluent, such as ethyl acetatelhexane (1:1) to provide the phthalimide derivative (13).

In Scheme II, step E, the phthalimide derivative (13) is converted to the primary amine (14). For example, phthalimide derivative (13) is combined with a suitable organic solvent, such as toluene and treated with an excess of hydrazine or a suitable hydrazine equivalent. The reaction mixture is stirred for about 45 minutes, heated at about 90° C. to about 95° C. until starting material disappears, cooled to about 0° C. and the primary amine (14) is collected by filtration.

In Scheme II, step F, the primary amine (14) is sulfonylated to provide sulfonamide (6) in a manner analogous to the procedure described in Scheme I, step D above.

In Scheme II, step G, the sulfonamide (6) is reduced to provide the free base (8) in a manner analogous to the procedure described in Scheme I, step F above.

In Scheme II, step H, the free base (8) is treated with a 3,5-dibenzoyl chloride to provide the compound of formula Ia in a manner analogous to the procedure described in Scheme 1, step H.

In addition, in Scheme II, step A can be skipped and the acid (9) can be carried on directly to reduction step C. In this manner the compound of formula I is ultimately prepared.

The following examples are illustrative only and are not intended to limit the invention in any way. The reagents and starting materials are readily available to one of ordinary skill in the art. Unless indicated otherwise, the substituents are defined as hereinabove. It is understood by one of ordinary skill in the art that the (R) and (S) enantiomers of formula I can be prepared by starting with, for example, (R)-2-phenyl-1-propylamine or (S)-2-phenyl-1-propylamine, rather than the racemate of 2-phenyl-1-propylamine, or by resolving the compound of formula I using standard techniques well known in the art, such as those described by J. Jacques, et al., "Enantiomers, Racemates, and Resolutions", John Wiley and Sons, Inc., 1981. Examples of such resolutions include recrystallization techniques or chiral chromatography.

As used herein, the following terms have the meanings indicated: "eq" refers to equivalents; "g" refers to grams; "mg" refers to milligrams; "ng" refers to nanograms; "L" refers to liters; "mL" refers to milliliters; "µL" refers to microliters;

"mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "GC" refers to gas chromatography; "$R_f$" refers to retention factor; "δ" prefers to part per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "aq" refers to aqueous; "iPrOAc" refers to isopropyl acetate; "EtOAc" refers to ethyl acetate; "EtOH" refers to ethyl alcohol; "MeOH" refers to methanol; "MTBE" refers to tert-butyl methyl ether, "DEAD" refers to diethyl azodicarboxylate; "TMEDA" refers to N,N,N',N'-tetramethylethylenediamine, and "RT" refers to room temperature.

EXAMPLE 1

Prerparation of N-2-(4-N-(3,5-Difluorobenzamido) phenyl)propyl-2-propanesulfonamide.

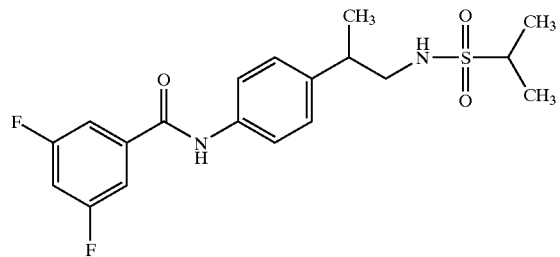

The title compound is prepared in a manner analogous to the procedure described at Example 196 in International Patent Application Publication WO 98/33496 published Aug. 6, 1998 from 3,5-difluorobenzoyl chloride.

Alternatively, the title compound can be prepared in a manner analogous to the procedures described generally in Schemes I and II, and more specifically as described in examples 2 and 3 below without employing the resolution steps as would be appreciated by one of ordinary skill in the art.

More specifically, into a 500 mL 3-neck flask fitted with a stirrer and thermometer, 3,5ifluorobenzoyl chloride (1.13 g) was added dropwise to a stirred solution of [2-(4-aminophenyl)propyl][(methylethyl)sulfonyl]amine (1.50 g) and triethylamine (625 mg) in methylene chloride (200 mL) at room temperature and under a nitrogen atmosphere. After stirring one hour at this temperature, TLC showed that the starting aniline had been consumed. The organic layer was washed once with water, dried over potassium carbonate, and concentrated under reduced vacuum to yield the crude material (2.61 g) as a solid. This crude material was purified by recrystallization from hexane/ethyl acetate 1:1 to yield the title compound (1.64 g, 71%)) as yellow crystals. M.P. 158° C.–160° C.

Ion spray M.S. 397.1 (M*+1). Calculated for $C_{19}H_{22}N_2O_2SF_2$—$H_2O$: Theory: C 55.03, H 5.83, N 6.76; Found: C 54.63, H 5.84, N 6.61.

EXAMPLE 2

Preparation of N-[4-((1R)-1-methyl-2-{[(methylethyl)sulfonyl]amino}ethyl)phenyl](3,5-difuorophenvl)carboxamide

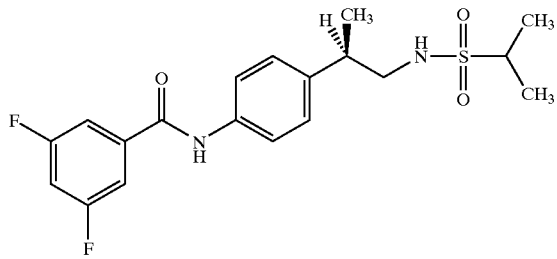

Preparation of 2-Phenyl-1-Propylamine HCl

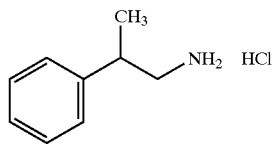

Scheme I, step A: To an autoclave hydrogenation apparatus under nitrogen was charged water-wet 5% palladium on carbon (453 g), ethanol (6.36 L), 2-phenylpropionitrile (636 g, 4.85 moles) and finally concentrated (12M) hydrochloric acid (613 g, 5.6 mole). The mixture was stirred rapidly and pressurized to 75–78 psi with hydrogen. The mixture was then heated to 50–64° C. for 3 hours. $^1$H NMR analysis of an aliquot showed less than 5% starting material. The reaction mixture was depressurized and filtered to afford two lots of filtrate that were concentrated under reduced pressure to ~400 mL each. To each lot was added methyl tert-butyl ether (MTBE) (2.2 L each) and the precipitated solids were allowed to stir overnight. Each lot was filtered and the collected solids were each washed with fresh MTBE (100 mL) and dried overnight. The lots were combined to afford 2-phenyl-1-propylamine HCl (634.4 9, 76.2%) as a white powder.

$^1$H NMR analysis of the free base: $^1$H NMR (CDCl$_3$, 300 MHz) δ 7.32 (m, 2H), 7.21 (m, 3H), 2.86 (m, 2H), 2.75 (m, 1H), 1.25 (d, 3H, J=6.9), 1.02 (br s, 2).

Preparation of (2R)-2-phenyliropylamine Malate

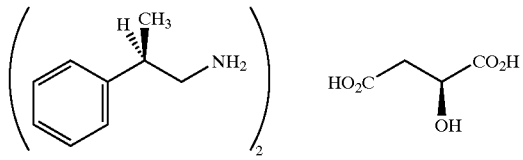

Scheme I, step B: To a dry 3-Liter round bottom flask under nitrogen was charged 2-phenyl-1-propylamine HCl (317.2 g, 1.85 moles), dry ethanol (2.0 L) and NaOH beads (75.4 g, 1.89 moles) that were washed in with additional ethanol (500 mL). The mixture was stirred for 1.6 hours, and the resulting milky white NaCl salts were filtered. An aliquot of the filtrate was analyzed by gas chromatography to provide the amount of free amine, 2-phenyl-1-propylamine, (1.85 moles). A solution of L-malic acid (62.0 g, 0.462 mole, 0.25 equivalents) in ethanol (320 mL) was added dropwise to the yellow filtrate and the solution was heated to 7520 C. The solution was stirred at 75° C. for 30 minutes. The heat was removed and the solution was allowed to cool slowly. The resulting thick precipitate was allowed to stir overnight. The precipitate was filtered and dried under vacuum after rinsing with ethanol (325 mL) to afford (2R)-2-phenylpropylamine malate (i47.6 g, 39.5%) as a white crystalline solid. Chiral GC analysis of the free base, 2-phenyl-1-propylamine revealed 83.2% e.e. enriched in the R-isomer (configuration was assigned via spectrometric comparison, via chiral HPLC, with commercially available (R)-2-phenyl-1-propylamine).

$^1$H NMR (CDCl$_3$, 300 MHz) δ 7.32 (m, 2H), 7.21 (m, 3H), 2.86 (m, 2H), 2.75 (m, 1H), 1.25 (d, 3H, J=6.9), 1.02 (br s, 2H).

A slurry of (2R)-2-phenylpropylamine malate (147.1 g, 83.2% e.e.) in 1325 mL ethanol and 150 mL deionized water was heated to reflux (~79.2° C.) until the solids went into solution. The homogeneous solution was allowed to slowly cool with stirring overnight. The precipitated white solids were cooled (0–5° C.) and filtered. The collected solids were rinsed with ethanol (150 mL) and dried at 35° C. to afford (2R)-2-phenylpropylamine malate (125.3 g, 85.2% recovery) as a white powder. Chiral GC analysis of the free base, (2R)-2-phenylpropylamine, revealed 96.7% e.e. enriched in the R-isomer.

$^1$H NMR (CD$_3$OD, 300 MHz) δ 7.32 (m, 10H), 4.26 (dd, 1H, J=3.6, 9.9), 3.08 (m, 6H), 2.72 (dd, 1H, J=9.3, 15.3), 2.38 (dd, 1H, J=9.3, 15.6), 1.33 (d, 6H, J=6.6).

Preparation of ((2R)-2-phenylpropyl)[(methylethyl)sulfonyl]amine

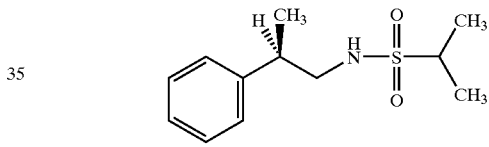

Scheme I, steps C and D: To a stirred slurry of (2R)-2-phenylpropylamine malate (200 g, 0.494 mol) in CH$_2$Cl$_2$ (1000 mL) was added 1.0 N NaOH (1050 mL, 1.05 moles). The mixture was stirred at room temperature for 1 hour and the organic phase was separated and gravity filtered into a 3.0 L round-bottom flask with a CH$_2$Cl$_2$ rinse (200 mL). The resulting free base, (2R)-2-phenylpropylamine, was dried via azeotropic distillation. Accordingly, the clear filtrate was concentrated to 600 mL at atmospheric pressure via distillation through a simple distillation head. Heptane (1000 mL) was added and the solution was concentrated again at atmospheric pressure to 600 mL using a nitrogen purge to increase the rate of distillation. The final pot temperature was 109° C.

The solution was cooled to room temperature under nitrogen with stirring to give a clear, colorless heptane solution (600 mL) of (2R)-2-phenylpropylamine. To this solution was added 4-dimethylaminopyridine (6.04 g, 0.0494 mol), triethylamine (200 g, 1.98 moles), and CH$_2$Cl$_2$ (500 mL). The mixture was stirred at room temperature until a clear solution was obtained. This solution was cooled to 50° C. and a solution of isopropylsulfonyl chloride (148 g, 1.04 moles) in CH$_2$Cl$_2$ (250 mL) was added dropwise with stirring over 2 hrs. The mixture was allowed to warrn gradually to room temperature over 16 h. GC analysis indicated complete consumption of the (2R)-2-phenylpropylamine starting material.

The stirred mixture was cooled to 8° C. and 2 N HCl (500 mL) was added dropwise. The organic phase was separated and extracted with water (1×500 mL) and saturated NaHCO$_3$ (1×500 mL). The organic phase was isolated, dried (Na$_2$SO$_4$), and gravity filtered. The filtrate was concentrated under reduced pressure to provide ((2R)-2-phenylpropyl)[(methylethyl)sulfonyl]amine (230 g, 96%) as a pale yellow oil. $^1$H NMR (CDCl$_3$, 300 MHz) δ 7.34 (m, 2H), 7.23 (m, 3H), 3.89 (br t, 1H, J=5.4), 3.36 (m,1H), 3.22 (m, 1H), 3.05 (m, 1H), 2.98 (m, 1H), 1.30 (d, 3H, J=7.2), 1.29 (d, 3H, J=6.9), 1.25 (d, 3H, J=6.9).

Preparation of [(2R)-2-(4-aminophenvy)propyl][(methylethyl)sulfony]amine p-toluenesulfonate

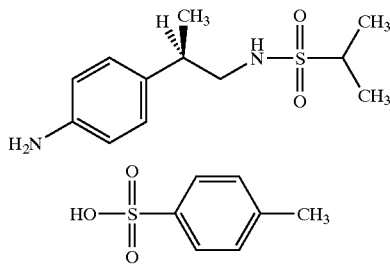

Scheme I, step E: To a round-bottom flask equipped with stir rod, thermocouple and nitrogen purge at 25° C., was charged ((2R)-2-phenylpropyl)[(methylethyl)sulfonyl]amine (5.00 g, 0.0207 mol), trifluoroacetic acid (15 mL), dichloromethane (1.2 mL) and heptane (8 mL). The mixture was cooled to −5° C. and 98% fuming nitric acid (1.60 g, 0.0249 mol) was added dropwise. The reaction mixture was stirred at −5 to +5° C. for 3–5 hours and then warmed to 20–25° C. The reaction was allowed to stir until GC analysis revealed that ((2R)-2-phenylpropyl)[(methylethyl)sulfonyl]amine is less then 1% (area %).

The reaction mixture was then diluted with dichloromethane (20 mL) and diionized water (20 mL), and the mixture was transferred to a suitably sized 3-neck bottom outlet round-bottom flask. The mixture was stirred for 10–15 minutes. The aqueous phase was separated, extracted with dichloromethane (10×20 mL), and the organic phases were combined. To the organic phase was added water (15 mL), 10% NaOH (10 mL), and the pH was adjusted to 6.5–7.5 with saturated sodium carbonate. After 10–15 mininutes of stirring, the organic layer was separated and concentrated to an oil under reduced pressure (25–35° C).

Scheme I, step F: The oil containing the mixture of [(2R)-2-(4-nitrophenyl)propyl][(methylethyl)sulfonyl]amine, [(2R)-2-(3-nitrophenyl)propyl][(methylethyl)sulfonyl]amine, and [(2R)-2-(2-nitrophenyl)propyl][(methylethyl)sulfonyl]amine, was diluted with ethanol and was transferred to a Parr bottle containing 1.25 g of 5% Pd on C (rinsed in with 5 mL of THF) under nitrogen (total ethanol=45 mL). The reaction mixture was hydrogenated for 16–20 hours at 20–25° C. until the GC area % of [(2R)-2-(4-aminophenyl)propyl][(methylethyl)sulfonyl]amine was greater than 70%. The reaction mixture was filtered through Hyflo followed by an ethanol rinse (25 mL).

The oil was diluted with THF (35 mL) and p-toluenesulfonic acid monohydrate (3.94 g, 0.0207 mol) was added with stirring at 20–25° C. When the solids completely dissolved, MTBE (22 mL) was added and the slurry was stirred for 1–2 hours. The slurry was filtered and the cake was rinsed three times with a 3:7 (v/v) solution of MBTE and THF. This process afforded [(2R)-2-(4-aminophenyl)propyl][(methylethyl)sulfonyl]amine p-toluenesulfonate in 53.5% yields as an off white powder. Chiral analysis of the freebase, [(2R)-2-(4-aminophenyl)propyl][(methyl ethyl)sulfonyl]amine, obtained extractively from [(2R)-2-(4-aminophenyl)propyl][(methylethyl)sulfony]amine ptoluenesulfonate, showed % e.e. of 99.5%.

$^1$H NMR (CD$_3$OD, 300 MHz) δ 7.70 (d, 2H, J=8.4), 7.43 (d, 2H, J=8.4), 7.33 (d, 2H, J=8.4), 7.23 (d, 2H, J=7.8), 3.22 (m, 2H), 3.08 (quint, 1H, J=6.9), 2.99 (g,1H, J=6.9), 1.29 (d, 3H, J=6.6), 1.23 (d, 3H, J=6.6).

Preparation of [(2R)-2-(4-aminophenyl)Propyl][(methylethyl)sulfonyl]amine

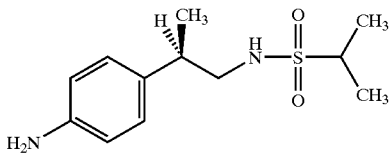

Scheme I, step G: To a suspension of [(2R)-2-(4-aminophenyl)propyg[(methylethyl)sulfonyl]amine p-toluenesulfonate (41.2 g, 0.0961 mol) in CH$_2$Cl$_2$ (300 mL) was added saturated aqueous NaHCO$_3$ until the pH of the aqueous phase was 6.5. The phases were separated and the organic phase was washed with 5% NaHCO$_3$ (2×100 mL), H$_2$O (100 mL), and concentrated to provide [(2R)-2-(4aminophenyl)propyll][(methylethyl)sulfonyl]amine as an oil. After diluting the oil with diethyl ether (50 mL), crystallization began after 10 min. Caution: Heat of crystallization caused ether to boil. After the exotherm subsided (45 minutes), the suspension was filtered, and the filter cake was washed with diethyl ether (2×20 mL), and dried under reduced pressure to afford [(2R)-2-(4-aminophenyl)propyl][(methylethyl)sulfonyl]amine (21.7 g, 88.1%). $^1$H NMR (CDCl$_3$, 300 MHz) δ 7.00 (d, 2H, J=8.1); 6.66 (d, 2H, J=8.4), 3.83 (m, (br s, 2H), 3.31 (m, 1H), 3.09 (m, 2H), 2.85 (m, 1H), 1.30 (d, 3H, J=7.2), 1.26 (d, 3H, J=6.9), 1.24 (d, 3H, J=6.9).

Preparation of N-[4-((1 R)-1-methyl-2-{[(methylethyl)sulfonyl]amino}ethyl)phenvyl](3,5difluoroihenyl)carboxamide, Method A Scheme I, step H: [(2R)-2-(4-aminophenyl)propyl][(methylethyl)sulfonylqamine p-toluenesulfonate (60.0 g, 0.140 mol), suspended in dichloromethane (375 mL), was treated with saturated aqueous NaHCO$_3$ in an amount sufficient to bring the salt into solution. The organic phase was separated and washed twice with aqueous NaHCO$_3$. HPLC analysis showed complete removal of p-toluenesulfonate from the organic phase. The organic phase was dried (MgSO$_4$), filtered, and chilled to −10° C. 3,5-difluorobenzoyl chloride (27.2 g, 0.154 mol) was added dropwise over 10 min and the mixture was allowed to warm to room temperature with stirring overnight.

After completion of reaction, the mixture was diluted with water (100 mL) and acetone (75 mL). The phases were separated, and the organic phase was washed with 0.1 N HCl (2×100 mL), 0.01 N NaOH (3×100 mL), and 0.1 N HCl (1×100 mL). The organic phase was separated and concentrated to a solid. The solid was resuspended in ethyl acetate and co-evaporated twice with ethyl acetate (2×60 mL) to remove traces of dichloromethane. The residue was transferred to a 500 mL flask with ethyl acetate (150 mL) and this mixture was heated to reflux to afford a clear solution. The solution was allowed to cool to room temperature over 5 hours, and the suspension was left to stir slowly overnight. The suspension was cooled to 0° C. and stirred for 1 hour. The product was collected by filtration and was vacuum dried to afford N-[4-((1 R)-1-methyl-2{[(methylethyl)sulfonyl]amino}ethyl)phenyl](3,5-difluorophenyl)carboxamide (43.9g, 79.0%) as a white crystalline solid.

¹H NMR (CDCl₃, 300 MHz) δ 7.80 (s, 1H), 7.59 (d, 2H, J=8.4), 7.40 (m, 2H), 7.23 (d, 2H, J=8.7), 7.01 (tt, 1H, J=2.1, 8.7), 3.87 (dd, 1H, J=5.1, 7.5), 3.36 (m,1H), 3.21 (m, 1H), 3.09 (m, 1H), 2.98 (m, 1H), 1.32 (d, 3H, J=6.6), 1.30 (d, 3 H, J=7.2) 1.28 (d, 3H, J=6.6).

Preparation of N-[4-((1 R)-1-methyl-2-{ [(methylethyl)sulfonyl]amino)ethyl)phenyl](35-difluorophenyl)carboxamide, Method B.

Scheme I, step H: To a 0° C. solution of [(2R)-2-(4-aminophenyl)propyl][(methylethyl)sulfonyl]amine (21.5 g, 0.0838 mol) and triethylamine (9.75 g, 13.4 mL, 0.0964 mol) in CH₂Cl₂ (86 mL) was added 3,5-difluorobenzoyl chloride (16.3 g, 0.0922 mol) dropwise over 30 min. After the addition was complete, the reaction mixture was stirred at 20° C. for 1 hour. The reaction mixture was washed with deionized water (2×100 mL) and 0.1 N HCl (2×100 mL). The organic phase was diluted with acetone (50 mL) to ensure complete dissolution of the product and the organic phase was washed with saturated K₂CO₃ (100 mL), 0.1 N HCl (100 mL), dried (MgSO₄, 3 g), filtered and co-evaporated with EtOAc to afford an oil. This oil was diluted with diethyl ether (125 mL), which induced crystallization. The solids were collected by filtration, washed with diethyl ether (2×20 mL), and dried under reduced pressure at room temperature overnight to afford N-[4-((1R)-1-methyl-2-{[(methylethyl)sulfonyl]amino}ethyl)phenyl](3,5-difluorophenyl)carboxamide (31.8 g, 95.7%) as a white crystalline powder.

An analytical sample was prepared via recrystallization from EtOAc. Thus, a clear solution of N-[4-((1R)-1-methyl-2-{[(methyiethyl)sulfonyl]amino}ethyl)phenyl](3,5difluorophenyl)carboxamide (28 g) was achieved in refluxing EtOAc (90 mL, minimum amount). This solution was allowed to cool over 2 hour to room temperature without stirring. The resulting dense mass was pulvarized with a glass rod and recovered by filtration. The collected solids were reslurried in diethyl ether, filtered and dried under reduced pressure to afford N-[4-((1R)-1-methyl-2-{ [(methylethyl)sulfonyl]amino}ethyl)phenyl](3,5-difluorophenyl)carboxamide (22.2 g, 79% recovery) as a white crystalline powder.

In addition, the final title compound, N-[4-((1R)-1-methyl-2-{[(methylethyl)sulfonyl]amino}ethyl)phenyl](3,5-difuorophenyl)carboxamide, can be jet milled by one of ordinary skill in the art, for example, with a Model 4 SDM Micronizer by Sturtevant Inc. to provide compound with a mean particle size of about 5.5 microns.

EXAMPLE 3

Alternative Preparation of N-]4-((1R)-1-methyl-2-{ [(methylethyl)sulfonyl]amino}ethyl)phenyl](3,5-difluorophenyl)carboxamide Preparation of (2R)-2-(4-nitrophenyl)propanoic Acid, S(-)α-methylbenzylamine

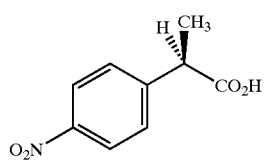
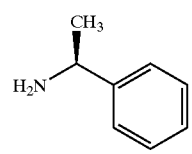

Scheme II, step A: A 2 liter three necked flask equipped with a mechanical stirrer is charged with racemic 2-(4-nitrophenyl)propionic acid (40.55 grams, 0.208 mol) and ethyl acetate (1600.0 mL). To this solution at 30° C. was then added S(-)α-methylbenzylamine (13.49 mL, 0.104 mol) all at once. Reaction exothermed to 38° C. with massive formation of a white precipitate in less than 15.0 minutes. The reaction mixture was then heated at ethyl acetate reflux for 10.0 minutes and allowed to equilibrate to room temperature with stirring overnight. The precipitate was then filtered to give a semi-dried white product, (2R)-2-(4-nitrophenyl)propanoic acid, S(-)α-methylbenzylamine (wet cake=25.43 grams). Reslured the wet cake in ethyl acetate (1600.0 mL) at reflux for 10.0 minutes, stirred to room temperature overnight, and filtered the white precipitate, (2R)-2-(4-nitrophenyl)propanoic acid, S(-)α-methylbenzylamine, (wet cake=21.02 grams, ee=91.4%). Repeated the later again and dried the precipitate at 40° C. in a vacuum oven for 24.0 hours, (2R)-2-(4-nitrophenyl)propanoic acid, S(-)-α-methylbenzylamine, (18.02 g, 55%, ee=95%); ¹H nmr (DMSO, 300 MHz) δ 1.31–1.32 (d, 3H), 1.37–1.38 (d, 3H), 3.56–3.60 (m, 1H), 4.184–20 (m, 1H), 7.27–7.53 (aromatic, 7H), 8.09–8.12 (aromatic, 2H); ¹³C nmr (DMSO, 300 MHz)) δ 19.91, 22.93, 48.45, 50.55, 123.71, 124.15, 127.15, 128.27, 129.06, 129.41, 129.76, 146.31, 153.36, 176.24.

Preparation of (2R)-2-(4-nitroihenyl)propanoic Acid.

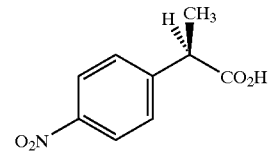

Scheme II, step B: To reaction mixture of (2R)-2-(4-nitrophenyl)propanoic acid, S(-)α-methylbenzylamine (56.04 g, 0.177 moles) in methylene chloride (400.0 mL) at room temperature was added 1 N HCl (300.0 mL) all at once with stirring for 45.0 minutes. The lower organic layer was then separated, dried with anhydrous magnesium sulfate, filtered, and concentrated under reduced pressure to afford the title compound, (2R)-2-(4-nitrophenyl)propanoic acid, (34.58 g, 100%) as an oil.

Preparation of (2R)-2-(4-nitrophenyl)propan-1-ol

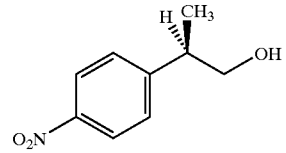

Scheme II, step C: A 500 ml three necked round bottom flask equipped with a mechanical stirrer, thermometer, addition funnel, reflux condenser and a continuous nitrogen purge is charged with (2R)-2-(4-nitrophenyl)propanoic acid (8.12 g, 41.6 mmol) and THF (120.0 mL). To this solution was added 10.0M borane dimethylsulfide (10.56 ml, 105.66 mmol) over a period of 30.0 minutes at room temperature. Reaction is quite exothermic with evolution of gas (exotherm can be controlled by the rate of addition of borane solution). The reaction is then refluxed for 5.0 hours, brought to room temperature and then quenched very carefully with saturated potassium carbonate solution (100.0 mL). Foaming observed during the quench can be controlled by the rate of addition of the carbonate solution. After 3.0 hours of stirring, the top organic layer is separated and the aqueous layer back extracted with methylene chloride (130.0 mL). The combined organic layer is then washed with saturated brine (100.0 mL), dried over anhydrous magnesium sulfate, filtered, and concentrated under reduced pressure at 50° C. to afford (2R)-2-(4-nitrophenyl)propan-1-01 (7.24 g, 96%); 1H nmr (CDCl$_3$, 300 MHz) δ 1.29 (d, 3H, J=7.02Hz), 1.69 (b. triplet, OH), 3.05 (m, 1H), 3.72 (m, 2H), 7.39 (d, 2H), 8.15 (d, 2H); $^{13}$C nmr (CDCl$_3$, 300 MHz) δ 17.61, 25.82, 42.61, 68.17, 123.92, 128.61, 146.90, 152.24.

Preparation of 2-[(2R)-2-(4-nitroihenyl)propyl] isoindoline-1,3-dione

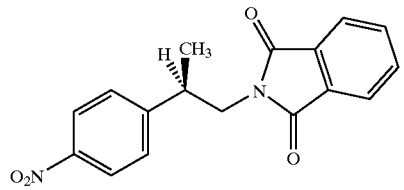

Scheme II, step D: A 250 mL three necked round bottom flask equipped with a mechanical stirrer, addition funnel, thermometer, and a reflux condenser is charged with (2R)-2-(4-nitrophenyl)propan-1-ol (2.0 g, 11.04 mmol), phthalimide (1.62 g, 11.04 mm), triphenylphosphine (4.3 g, 16.59 mmol) and THF (50.0 mL) at room temperature. To this solution was added DEAD (2.6 mL, 16.59 mmol) over a period of 5 minutes (reaction exothermed to reflux by the end of addition). The reaction was then stirred to room temperature overnight for convenience, quenched with water (50.0 mL) and extracted organic with methylene chloride (50.0 mL). The organic layer was then dried with anhydrous magnesium sulfate, filtered, and concentrated under reduced pressure at 50° C. to an oil (11.62 g). Plug filtration of the oil over silica gel with 1:1 ethyl acetate/hexane (470.0 mL) and subsequent concentration of the fractions containing product afforded a light yellow precipitate. The precipitate was then dried in a house vacuum at 40° C. to provide 2-[(2R)-2-(4-nitrophenyl)propyt]isoindoline-1,3-dione (3.32 g, 96.9%); $^1$H nmr (CDCl$_3$, 300 MHz) δ 1.50 (d, 3H, J=6.74Hz), 3.45 (m, 1H), 3.89–3.95 (m, 2H) 7.5 (d, 2H), 7.67 (m, 2H), 7.68 (m, 2H), 8.10 (d, 2H); $^{13}$C nmr (CDCl$_3$, 300 MHz) δ 19.21, 38.90, 44.45, 123.59, 123.99, 128.50, 131.86, 134.35, 151.13, 168.34.

Preparation of (2R)-2-(4-nitrophenyl)propylamine

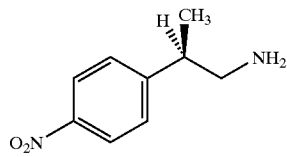

Scheme II, step E: A 250 mL three necked round bottom flask equipped with a mechanical stirrer, thermometer, reflux condenser and addition funnel is charged with 2-[(2R)-2-(4-nitrophenyl)propyl]isoindoline-1,3-dione (25.02 g, 80.6 mmol) and toluene (200.0 mL). To this solution at room temperature was added anhydrous hydrazine (7.08 mL, 226.0 mmol). Reaction exothermed slightly and was stirred for 45 minutes, heated at 90° C.–95° C. until the disappearance of starting material. A massive precipitate formed by the end of the reaction. Cooled to room temperature and chilled to 0° C. before filtration. Concentration of the filtrate afforded (2R)-2-(4-nitrophenyl)propylamine (14.11 g, 97%) as an oil;

$^1$H nmr (CDCl$_3$, 300 MHz) δ 1.01 (b, 1H), 1.27 (d, 3H, J=6.4Hz), 2.87 (m, 2H), 7.36 (d, 2H), 8.14 (d, 2H); $^{13}$C nmr (CDCl$_3$, 300 MHz) 819.03, 43.51, 49.21, 123.67, 128.09, 153.04.

Preparation of [(2R)-2-(4-nitroihenyl)propyl] [(methylethyl)sulfonyl]amine

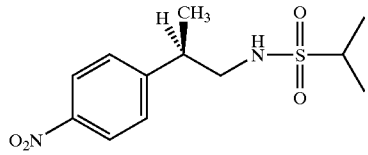

Scheme II, step F: A 500 mL three necked round bottom flask equipped with a mechanical stirrer, thermometer and an addition funnel is charged with (2R)-2-(4-nitrophenyl) propylamine (11.75 g, 65.21 mmol), methylene chloride (150.0 mL) and triethylamine (18.2 mL, 130.4 mmol). To this solution at 0° C. was added isopropylsulfonyl chloride (8.92 mL, 63.9 mmol) over a period of 20 minutes. Reaction was then stirred to room temperature overnight, then quenched with 1N HCl (150.0 mL). The lower organic layer is separated and dried with anhydrous magnesium sulfate, filtered, and concentrated under reduced pressure to afford [(2R)-2-(4-nitrophenyl)propyl][(methylethyl)sulfonyl] amine (14.11 g, 97%) as an oil; $^1$H nmr (CDCl$_3$, 300 MHz) δ 1.26 (d, 3H, J=6.7Hz), 1.31 (d, 6H), 3.06 (m, 1H), 3.30 (m, 1H), 4.25 (broad triplet, 1H), 7.38 (d, 2H), 8.10 (2H); $^{13}$C nmr (CDCl$_3$, 300 MHz) δ 16.75, 18.95, 41.29, 50.15, 53.85, 124.22, 128.52, 151.26.

Preparation of [(2R)-2-(4-nitrophenyl)propyl] [(methllethyl)sulfonyl]amine

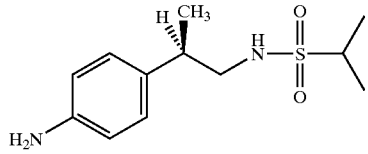

Scheme II, step G: A 500 mL parr bottle is charged with [(2R)-2-(4-nitrophenyl)propyq[](methylethyl)sulfonyl] amine (14.45 g, 50.60 mmol), 3A EtOH (80.0 mL) and 10% P/C (4.0 g). The reaction mixture was then hydrogenated at room temperature and at 55 psi for 6 hours. Filtered reaction mixture over hyflo and washed cake with 3A EtOH (100.0 mL). The filtrate was then concentrated at reduced pressure to provide [(2R)-2-(4-nitrophenyl)propyl][(methylethyl) sulfonyl]amine (12.97 g, 100%) as an oil; $^1$H nmr (CDCl$_3$, 300 MHz) δ 1.26 (d, 3H, J=6.7Hz), 1.31 (d, 6H), 2.4 (m, 1H), 3.0–2H), 3.2–3.4 (m, 1H), 4.0 (b, 1H), 4.6 (b,2H), 6.61 (d, 2H), 7.0 (d, 2H).

Preparation of N-[-4-((1R)-1-methyl-2-{[(methylethyl)sulfonyl]amino}ethyl)phenyl](3,5-difluorophenyl)carboxamide

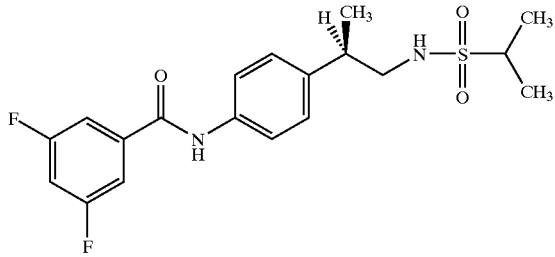

Scheme II, step H: A 500 mL three necked round bottom flask equipped with a magnetic stirrer, thermometer, addition funnel and a positive nitrogen was charged with [(2R)-2-(4-nitrophenyl)propyl][(methylethyl)sulfonyl]amine (12.02 g, 46.85 mmol) and methylene chloride (200.0 mL). To this solution was added triethylamine (6.53 mL, 46.85 mmol) all at once. The solution was stirred for 10 minutes then added dropwise, neat 3,5difluorobenzoyl chloride (5.9 mL, 46.85 mmol) over a period of 20 minutes. The reaction exothermed to reflux by the end of addition. Stirred to room temperature over the weekend for convenience. Quenched reaction with 1 N HCl (100.0 mL) and separated lower organic layer. Washed the organic layer with 25% brine (70.0 mL) and dried with anhydrous magnesium sulfate. Filtered precipitates and concentrated filtrate to a tan oil (20.0 g). To this oil was added 1:1 ethyl acetate/hexane (125.0 mL) with stirring. A massive off white precipitate formed. The precipitate was then filtered and the cake washed with 1:1 ethyl acetate/hexane (50.0 mL). Precipitate was then dried in a house vacuum oven at 40° C. to provide N-[4-((1R)-1-methyl-2-{[(methylethyl)sulfonyl]amino}ethyl)phenyl](3,5-difluorophenyl)carboxamide (15.02 g, 80.9%); $^1$H NMR (CDCl$_3$, 300 MHz) δ 1.26–1.27 (d, 6H), 1.29–1.30 (d, 2H), 2.92 (m, 1H), 3.10 (m, 1H), 3.20 (1H), 3.3–3.4 (m, 1H), 7.0 (triplet, 1H), 7.20 (d, 2H), 7.40 (d, 2H), 7.60 (m, 2H), 8.19 (s, 1H); $^{13}$C NMR (CDCl$_3$, 300 MHz) δ 17.19, 17.30, 19.75, 41.03, 50.99, 54.15, 107.68, 107.86, 108.08, 111.12, 111.33, 121.81, 128.59, 136.97, 138.77, 140.51, 162.62, 162.71, 164.12, 164.61, 164.71.

EXAMPLE 4

Alternative preparation of [(2R)-2-(4-aminophenyl)propyl][(methylethyl)sulfonyl]amine p-toluenesulfonate

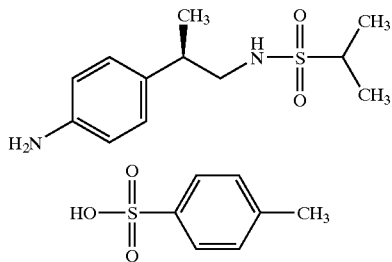

To a mechanically stirred solution of 2-phenyl-1-propylamine amine (50.0 g, 0.370 mol, can be prepared in a manner analogous to the procedure disclosed by A. W. Weston, et al., *J. Am. Chem. Soc.*, 65, 674 (1943)) in 90% ethanol/H$_2$O (denatured with 0.5% toluene) (450 mL) was added L-malic acid (24.8 g, 0.185 mol) portionwise at room temperature with a 90% ethanol/H$_2$O rinse (50 mL) to give a clear solution after a mild exotherm. This solution was allowed to cool and a white precipitate appeared after 30 min. The precipitation was allowed to proceed with slow stirring overnight. The resulting slurry was suction is filtered (buchner funnel) and rinsed with 100% ethanol (denatured with 0.5% toluene) (2×100 mL) to afford, after air-drying, 30 g of (2R)-2-phenylpropylamine malate as a white solid. Chiral chromatographic analysis of the isopropylsulfonamide derivative of the free base indicated 84% ee.

This (2R)-2-phenylpropylamine malate (30 g) was suspended in 90% ethanol/H$_2$O (300 mL) and heated to 78° C. with slow stirring to afford a clear colorless solution. The solution was allowed to cool slowly to room temperature overnight. Precipitation commenced at 60–65° C. The solids were filtered and rinsed at room temperature with 100% ethanol (2×50 mL) to give (2R)-2-phenylpropylamine malate (24.3 g, 32%) as a white crystalline solid. Chiral chromatographic analysis of the isopropylsulfonamide derivative of the free base indicated 96.5% ee.

Preparation of (2R)-2-phenylropylamine

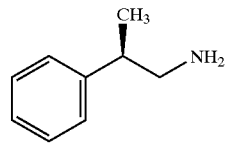

To a stirred suspension of (2R)-2-phenylpropylamine malate (24.3 g, 0.0601 mol, prepared directly above) in CH$_2$Cl$_2$ (200 mL) was added 1.0 N NaOH dropwise at room temperature. The organic phase was isolated, extracted with brine (1×125 mL), dried (Na$_2$SO$_4$), filtered, and concentrated under reduced pressure to give (2R)-2-phenylpropylamine (19 g) as a clear, colorless oil.

Preparation of ((2)-2-phenylpropyl)[(methylethyl)sulfonyl]amine

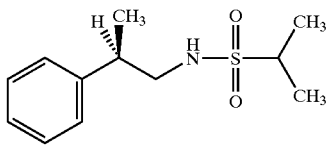

Scheme I, step A: To a stirred 2° C. solution of (2R)-2-phenylpropylamine (0.12 mol) and triethylamine (24.3 g, 0.240 mol) in CH$_2$Cl$_2$ (140 mL) under nitrogen, was added a solution of isopropylsulfonyl chloride (97%) (16.3 g, 0.118 mol) in CH$_2$Cl$_2$ (20 mL) dropwise while maintaining the reaction temperature below 15° C. Residual isopropylsulfonyl chloride was rinsed in with CH$_2$Cl$_2$(10 mL). This solution was stirred at 0° C. for 1 hour and was then allowed to warm to room temperature overnight.

The reaction mixture was re-cooled to 0° C. before adding 1 N HCl (125 mL) dropwise with stirring. The organic phase was then isolated and washed with saturated aqueous NaHCO$_3$ (1×125 mL) and the organic phase was separated, dried (MgSO$_4$), and filtered. The filtrate was concentrated under reduced pressure to afford ((2R)-2-phenylpropyl)[(methylethyl)sulfonyl]amine (25.76 g, 90%) as a yellow oil.

Preparation of [(2R)-2-(4-aminophenyl)propyl][(methllethyl)sulfonyl]amine p-toluenesulfonate To a room temperature solution of ((2R)-2-phenylpropyl)[(methylethyl)sulfonyl]amine (43.3 g, 0.179 mol) in trifluoroacetic acid (344 mL) was added NaNO$_3$ (45.7 g, 0.538 mol), and the resulting reaction mixture was stirred for 5 hours. The reaction mixture was diluted with CH$_2$Cl$_2$ (1 L), and washed with H$_2$O (2×300 mL), and separated. The organic phase was diluted again with H$_2$O (150 mL), and the heterogeneous mixture was neutralized with solid NaHCO$_3$ until the aqueous layer was pH 5.7. The organic phase was concentrated to an oil (43 g) that was dissolved in 3A ethanol (250 mL). The solution was then hydrogenated overnight at 50–60 psi over 7 g of 5% palladium on carbon.

$^1$H NMR analysis of a reaction aliquot indicated complete reduction and 70% para isomer in the regioisomeric mixture. The mixture was filtered through Celitee®, and the filtrate was concentrated to an oil (41 g, 0.160 mol) that was subsequently diluted with THF (125 mL). This THF solution was added to a solution of p-toluenesulfonic acid monohydrate (37 g, 0.195 mol) in a 1:1 (v/v) THF/diethyl ether solution. Diethyl ether was added to this clear solution until the onset of cloudiness. After about 10 minutes, solids precipitated as a dense unstirrable mass. The mixture was diluted further with diethyl ether (300 mL) and THF (350 mL), and the resulting suspension was filtered. The filter cake was washed with 2:5 (v/v) THF/diethyl ether (3×80 mL) and the cake was dried under reduced pressure to afford [(2R-(2-(4-aminophenyl)propyl][(methylethyl)sulfonyl] amine p-toluenesulfonate (41.7 g, 54%) as a white powder.

EXAMPLE 5

Alternative preparation of ((2R)-2-phenvliropyl)[(methylethyl)sulfonyl]amine

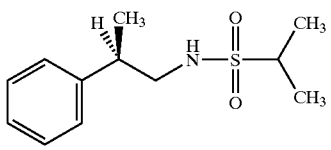

Preparation of (2R)-2-phenylpropan-1-ol

An oven dried 500.0 mL three necked round bottom flask equipped with a mechanical stirrer, thermometer, addition funnel with a continuous nitrogen blanket is charged with 2.0 M solution of trimethylaluminum (65.6 mL, 131.2 mmol) and toluene (75.0 mL). Reaction solution was then chilled to −60° C. with dry ice/acetone bath. To this solution was then added R-styrene oxide dissolved in 100.0 mL of toluene over a period of 50.0 minutes (reaction is quite exothermic and can be controlled by the rate of addition of substrate). After stirring at this temperature for 60.0 minutes, reaction was brought to room temperature and stirred for 4.0 hours. Reverse quenched reaction at room temperature into a slurry of THF (100.0 mL) and sodium sulfate decahydrate (46.0 g) very cautiously over a period of 90.0 minutes (quenching was quite exothermic with evolution of gas). Filtered the precipitate formed over hyflo, then concentrated filtrate to provide the intermediate title compound, (2R)-2-phenylpropan-1-ol, (11.03 g, 92.6%) as an oil; $^1$H nmr (CDCl$_3$, 300 MHz) δ 1.28–1.29 (d, 3H, J=6.9Hz), 1.5 (b, 1H), 2.9–3.0 (m, 1H), 3.69–3.70 (d, 2H, J=6.64Hz), 7.24–7.35 (aromatic); $^1$ nmr (CDCl$_3$, 300 MHz) δ 18.31, 43.15, 69.40, 127.38, 128.20, 129.26144.39.

Preparation of 2-((2R)-2-phenylpropyl)isoindoline-1.3-dione

An oven dried 250.0 mL three necked round bottom flask equipped with a mechanical stirrer, thermometer, addition funnel with a continuous nitrogen blanket is charged with (2R)-2-phenylpropan-1-ol (2.0 mL, 14.32 mmol), phthalimide (2.1 g, 14.32 mmol), triphenylphosphine (5.63 g, 21.48 mmol) and THF (70.0 mL). To this solution at room temperature was then added a solution of diethylazodicarboxylate (3.38 mL, 21.48 mmol) dissolved in THF (10.0 mL) over a period of 15–20 minutes (reaction exothermed slightly to 50° C. by the end of addition went from clear to reddish color). Stirred reaction to room temperature overnight). To the red solution was added water (50.0 mL) and the organic extracted with chloroform (140.0 mL). Dried the organic solution with anhydrous magnesium sulfate, filtered and concentrated under reduced pressure to an oil. To the oil was added heptane (150.0 mL) with stirring. Filtered of precipitates, then concentrated filtrate to an oil. Plug filtration of the oil over silica gel with 1:1 ethylacetate/hexane and concentrating product fractions afforded the intermediate title compound, 2-((2R)-2-phenylpropyl)isoindoline-1,3-dione, (4.27 g, 96%) as an oil which solidified on equilibrating to room temperature; $^1$H nmr (CDCl$_3$, 300 MHz) δ 1.3 (d, 3H), 3.3–4.0(m, 1H), 3.7–3.9 (m, 2H), 7.1–7.3 (aromat. m, 2H), 7.63–7.7 (aromat. m, 2H), 7.8–7.85 (aromat. m, 4H).

Preparation of (2R)-2-phenylpropylamine

A 500 mL three necked round bottom flask equipped with a mechanical stirrer, thermometer and addition funnel is charged with 2-((2R)-2-phenylpropyl)isoindoline-1,3-dione (11.54 g, 43.49 mmol), toluene (200.0 mL) and anhydrous hydrazine (2.73 mL, 86.99 mmol). Reaction is then stirred at room temperature for 3.0 hours and then heated at 90° C.–95° C. for 2.0 hours. Cooled the slurry to room temperature, filtered precipitates, then concentrated filtrate to provide the intermediate title compound, (2R)-2-phenylpropylamine, (5.58 g, 94.9%) an oil; $^1$H nmr (CDCl$_3$, 300 MHz) δ 1.21 (d, 3H), 1.40–1.60 (b, 2H), 2.68–2.80 (m, 1H), 2.81–2.87 (m, 2H) 7.20 (m, 2H), 7.32 (m, 2H).

Preparation of Final title Compound

To a solution of the (2R)-2-phenylpropylamine (1.2g, 8.87mmol) in hexane (16.0 mL) was added triethylamine (2.47 mL, 17.74 mmol) and dimethylaminopyridine (0.30 g, 2.47 mmol). Cooled reaction to 5° C., then added a solution of isopropylsulfonyl chloride (0.97 mL, 8.69 mmol) dissolved in methylene chloride (6.0 mL) over a period of 15.0 minutes. Stirred for 45.0 minutes, then stirred at room temperature for 120.0 minutes. Quenched reaction with IN HCl (20.0 mL) and extracted organic with methylene chloride (25.0 mL). Dried organic layer with anhydrous magnesium sulfate, filtered and concentrated filtrate to provide the final title compound, ((2R)-2-phenylpropyl)[(methylethyl)sulfonyl]amine, (1.93 g, 90.1%) an oil; $^1$H nmr (CDCl$_3$, 300 MHz) δ 1.25 (d, 3H, J=6.9Hz), 1.29(d, 3H, J=6.9Hz), 1.30 (d, 3H, J=7.2 Hz), 2.98 (m, 1H), 3.05 (m, 1H), 3.22 (m, 1H), 3.36 (m, 1H), 3.89 (b, 1H), 7.23 (m, 2H), 7.34 (m, 2H).

The ability of compounds of formula I to potentiate glutamate receptor-mediated response may be determined using fluorescent calcium indicator dyes (Molecular Probes, Eugene, Oregon, Fluo-3) and by measuring glutamate-evoked efflux of calcium into GluR4 transfected HEK293 cells, as described in more detail below.

In one test, 96 well plates containing confluent monolayers of HEK 293 cells stably expressing human GluR4B (obtained as described in European Patent Application Publication Number EP-A1-583917) are prepared. The tissue culture medium in the wells is then discarded, and the wells are each washed once with 200 μl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 μM Fluo3-AM dye (obtained from Molecular Probes Inc., Eugene, Oreg.) in buffer in each well. After the incubation, each well is washed once with 100 pij buffer, 200 piI of buffer is added and the plates are incubated for 30 minutes.

Solutions for use in the test are also prepared as follows. 30 μM, 10 μM, 3 μM and 1 μM dilutions of test compound are prepared using buffer from a 10 μM solution of test compound in DMSO. 100 μM cyclothiazide solution is prepared by adding 3 μl of 100 mM cyclothiazide to 3 mL of buffer. Control buffer solution is prepared by adding 1.5 μl DMSO to 498.5 μl of buffer.

Each test is then performed as follows. 200 μl of control buffer in each well is discarded and replaced with 45μl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 μl of buffer and 45 μl of test compound in buffer in appropriate wells. A second fluorescent reading is taken after 5 minutes incubation. 15 μl of 400 μM glutamate solution is then added to each well (final glutamate concentration 100 μM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 μM cyclothiazide.

In another test, HEK293 cells stably expressing human GluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 MgCl$_2$, 2 CaCl$_2$, 10 glucose, pH=7.4 with NaOH, 295 mOsm kg−1. The intracellular recording solution contains (in mM): 140 CsCl, 1 MgCl$_2$, HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg−1. With these solutions, recording pipettes have a resistance of 2–3 MΩ. Using the whole-cell voltage clamp technique (Hamill et al.(1981))Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

It has been discovered that the compounds of formula Ia possess superior exposure properties. Such properties allow for enhanced exposure when compared to, for example:

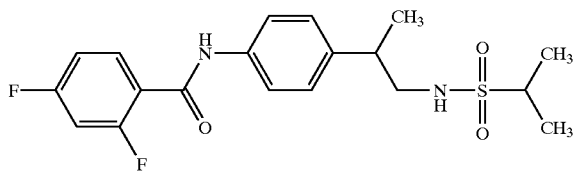

referred to herein as "N-[4-(1-methyl-2-{[(methylethyl) sulfonyl]amino}ethyl)phenyl](2,4-difluorophenyl) carboxamide" which is disclosed at Example 196 in International Patent Application Publication WO 98/33496 published Aug. 6, 1998. As a result, the disease being treated is more effectively managed. For example, a more effective management of the disease may be achieved with the administration of a compound of formula Ia, since dosing frequency may be reduced. By reducing dosing frequency, overnight treatment while the patient is asleep, for example, may be effected. Furthermore, lower dose frequency would facilitate patient compliance with the treatment regimen.

More specifically, Table I discloses the comparison of rat plasma concentrations for:

N-[4-(1-methyl-2-{[(methylethyl)sulfonyl]amino}ethyl) phenyl](2,4-difluorophenyl)carboxamide; and N-[4-((1R)-1-methyl-2{[(methylethyl)sulfonyl] amino}ethyl)phenyl](3,5-difluorophenyl)carboxamide.

General Procedure for Determination of Plasma Exposure of Test Compounds in Rats Each compound was administered as a suspension in a vehicle consisting of 5% ethanol, 95% of a mixture of 0.5% each Polysorbate 80/sodium carboxymethylcellulose in water. Three male F-344 rats were dosed orally at 30 mg/kg by gavage and blood collected by orbital venapuncture under isoflurane anesthesia at 0.5, 1, and 2 hours after dosing into sodium heparinized containers. The final 6 hour time-point was collected by cardiac puncture into sodium heparinized containers. Plasma was collected after brief centrifugation and frozen at −70° C. until assay. Plasma samples were assayed by LC/MS using standards prepared by spiking plasma with the compound of interest.

TABLE 1

Rat Plasma Concentrations After a 30 mg/kg Dose[1].

| Time(hr) | Concentration of A[2] ng/mL | Concentration of B[3] ng/mL |
|---|---|---|
| 0.5 | 473 ± 100 | 1491 ± 12 |
| 1 | 333 ± 53 | 1171 ± 134 |
| 2 | 329 ± 62 | 1035 ± 62 |
| 6 | 67 ± 17 | 693 ± 136 |

[1]n = 3
[2]A = N-[4-(1-methyl-2-{[(methylethyl)sulfonyl]amino}ethyl)phenyl](2,4-difluorophenyl)carboxamide.
[3]B = N-[4-((1R)-1-methyl-2-{[(methylethyl)sulfonyl]amino}ethyl)phenyl](3,5-difluorophenyl)carboxamide.

Table 2 discloses the area under the curve (AUC), the maximum concentration of test compound ($C_{max}$), and the time at which maximum concentration resulted ($t_{max}$) for:

N-[4-(1-methyl-2[(methylethyl)sulfonyl]amino}ethyl) phenyl](2,4-difluorophenyl)carboxamide; and N-[4-((1R)-1-methyl-2{[(methylethyl)sulfonyl] amino}ethyl)phenyl](3,5-difluorophenyl)carboxamide.

TABLE 2

Pharmacokinetic Parameters Obtained in Rats After Oral Administration of a 30 mg/kg Dose[1].

| | Compound A[2] | Compound B[3] |
|---|---|---|
| AUC (ng · hr/mL) | 1442 ± 227 | 5596 ± 14 |
| $C_{max}$ (ng/mL) | 473 | 1491 |
| $t_{max}$ | 0.5 | 0.5 |

[1]n = 3
[2]A = N-[4-(1-methyl-2-{[(methylethyl)sulfonyl]amino}ethyl)phenyl](2,4-difluorophenyl)carboxamide.
[3]B = N-[4-((1R)-1-methyl-2-{[(methylethyl)sulfonyl]amino}ethyl)phenyl](3,5-difluorophenyl)carboxamide.

According to another aspect, the present invention provides a pharmaceutical composition, which comprises a compound of formula Ia or a pharmaceutically acceptable salt thereof and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, is suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 150 micrograms to about 150 mg active ingredient, preferably about 150 micrograms to about 30 mg active ingredient, and most preferably about 150 micrograms to about 1 mg active ingredient. As used herein the term "active ingredient" refers to a compound included within the scope of formula I, such as N-[4-((1R)-1-methyl-2-{[(methylethyl)sulfonyl]amino}ethyl)phenyl](3,5difluorophenyl)carboxamide. The term "unit dosage form" refers to a physically discrete unit suitable as a unitary dosage for a patient, each unit containing a predetermined quantity of active ingredient calculated to produce the desired therapeutic effect, in association with a suitable pharmaceutical carrier, diluent, or excipient. The components of the formulation are brought together according to standard practice and procedures well known to one of ordinary skill in the art using conventional formulation andmanufacturing techniques. The following formulation examples are illustrative only and are not intended to limit the scope of the invention in any way. The reagents and starting materials are readily available to one of ordinary skill in the art.

Formulation

Hard gelatin capsules are prepared using the following ingredients to provide capsules containing 0.15 mg, 1 mg, 5 mg, and 30 mg of N-[4-((1R)-1-methyl-2{[(methylethyl)sulfonyl]amino}ethyl)phenyl](3,5-difluorophenyl)carboxamide:

| Component | mg/capsule | mg/capsule | mg/capsule | mg/capsule |
|---|---|---|---|---|
| N-[4-((1R)-1-methyl-2-{[(methylethyl)sulfonyl]amino}ethyl)phenyl](3,5-difluorophenyl)carboxamide | 0.15 | 1 | 5 | 30 |
| Lactose | 242.975 | 242.125 | 238.125 | 213.125 |
| Povidone | 2.5 | 2.5 | 2.5 | 2.5 |
| Polysorbate 80 | 2.5 | 2.5 | 2.5 | 2.5 |
| Magnesium Stearate | 1.875 | 1.875 | 1.875 | 1.875 |
| Total | 250 | 250 | 250 | 250 |

N-[4-((1R)-1-methyl-2{[(methylethyl)sulfonyl]amino}ethyl)phenyl](3,5-difluorophenyl)carboxamide is blended with lactose that is wet granulated using povidone and polysorbate 80. The wet granulation is then sized and dried. The dried granulation is milled and then blended with magnesium stearate. This final formulation is then filled into hard gelatin capsules.

As used herein the term "patient" refers to a mammal, such as a mouse, guinea pig, rat, dog or human. It is understood that the preferred patient is a human.

The term "treating" (or "treat") as used herein includes its generally accepted meaning which encompasses prohibiting, preventing, restraining, and slowing, stopping, or reversing progression of a resultant symptom. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease is involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances. For example, a typical daily dose may contain from about 150 micrograms to about 150 mg of the active ingredient. The compounds can be administered by a variety of routes including oral, rectal, transdermal, subcutaneous, intravenous, intramuscular, bucal or intranasal routes. Alternatively, the compound may be administered by continuous infusion.

We claim:

1. A compound of the formula:

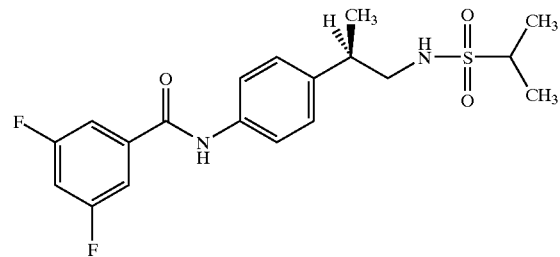

or a pharmaceutically acceptable salt thereof.

2. A compound of the formula:

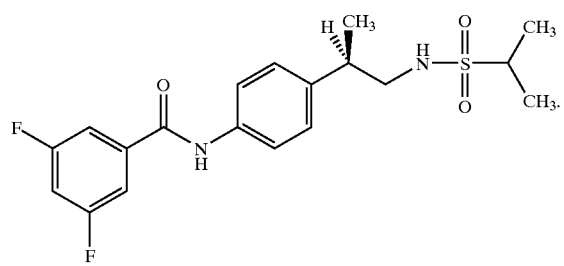

3. A composition comprising a compound of the formula:

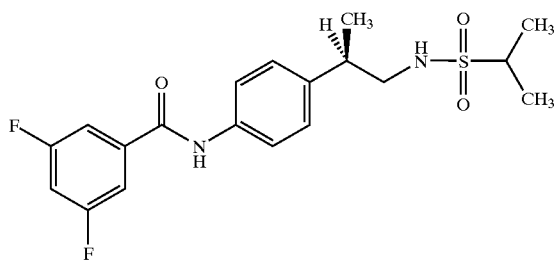

or a pharmaceutically acceptable salt thereof in combination with a pharmaceutically acceptable carrier, diluent or excipient.

4. A method of potentiating glutamate receptor function in a patient, which comprises administering to said patient an effective amount of a compound of the formula:

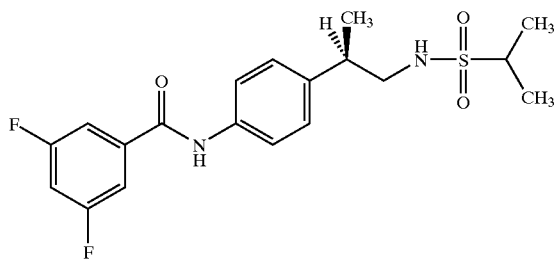

or a pharmaceutically acceptable salt thereof.

5. A method of treating depression in a patient comprising administering to said patient an effective amount of a compound of the formula:

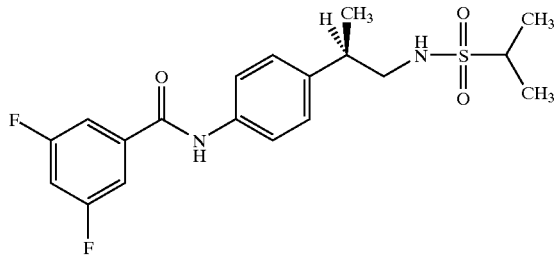

or a pharmaceutically acceptable salt thereof.

6. A method of treating schizophrenia in a patient comprising administering to said patient an effective amount of a compound of the formula:

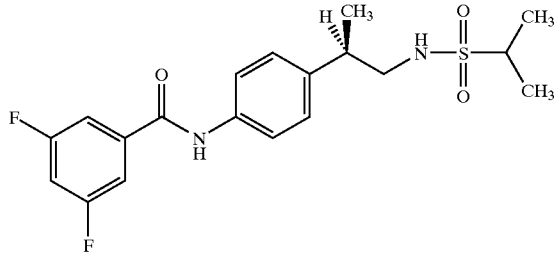

or a pharmaceutically acceptable salt thereof.

7. A method of treating cognitive disorders in a patient comprising administering to said patient an effective amount of a compound of the formula:

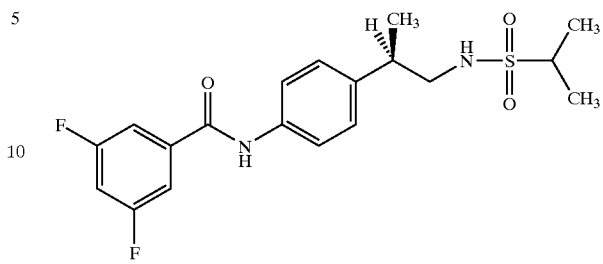

or a pharmaceutically acceptable salt thereof.

8. A process for the preparation of a compound of formula Ia:

formula Ia

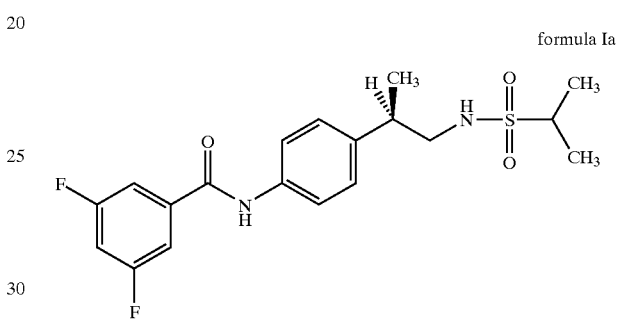

comprising, nitrating a sulfonamide (5):

(5)

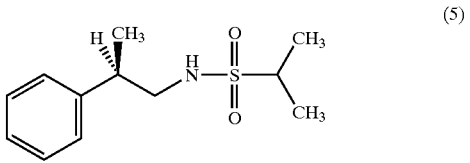

to provide a p-nitro derivative (6):

(6)

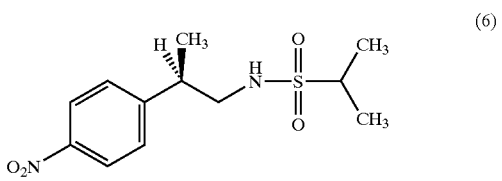

hydrogenating the p-nitro derivative (6) to provide a p-amino derivative (7):

(7)

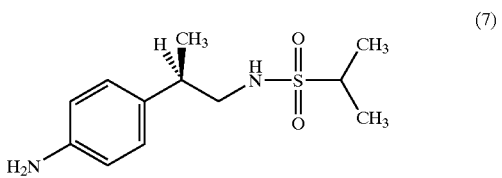

treating the p-amino derivative (7) with a suitable acid, then treating with a suitable base, and then treating with 3,5difluorobenzoyl chloride.-

9. An article of manufacture comprising packaging material and a compound of formula:

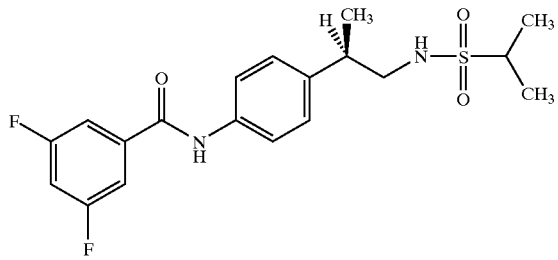

or a pharmaceutically acceptable salt thereof contained within said packaging material, wherein said packaging material comprises a label which indicates that said compound can be used for treating at least one of the following; Alzheimer's disease, schizophrenia, cognitive deficits associated with schizophrenia, depression, and cognitive disorders.

10. An article of manufacture according to claiam 9 wherein said label indicates that said compound can be used for treating Alzheimer's disease.

11. An article of manufacture according to claim 9 wherein said label indicates that said compound can be used for treating schizophrenia.

12. An article of manufacture according to claim 9 wherein said label indicates that said compound can be used for treating depression.

13. An article of manufacture according to claim 9 wherein said label indicates that said compound can be used for treating cognitive deficits associated with schizophrenia.

14. A method of treating Parkinson's disease in a patient comprising administering to said patient an effective amount of a compound of the formula:

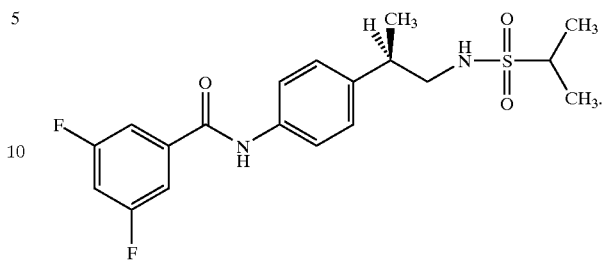

15. A method of treating Alzheimer's disease in a patient comprising administering to said patient an effective amount of a compound of the formula:

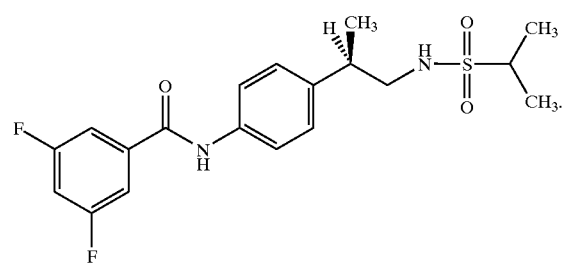

\* \* \* \* \*